United States Patent
Tempco et al.

(10) Patent No.: US 10,575,886 B2
(45) Date of Patent: Mar. 3, 2020

(54) BONE SCREW AND METHOD OF MANUFACTURE

(71) Applicant: Warsaw Orthopedic, Inc., Warsaw, IN (US)

(72) Inventors: Dale A. Tempco, Germantown, TN (US); Rodney Ray Ballard, Lakeland, TN (US); Keith E. Miller, Germantown, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/975,203

(22) Filed: May 9, 2018

(65) Prior Publication Data

US 2019/0343564 A1    Nov. 14, 2019

(51) Int. Cl.
*A61B 17/86* (2006.01)
*B33Y 80/00* (2015.01)
*A61B 17/00* (2006.01)

(52) U.S. Cl.
CPC .......... *A61B 17/864* (2013.01); *A61B 17/863* (2013.01); *A61B 17/866* (2013.01); *B33Y 80/00* (2014.12); *A61B 2017/00526* (2013.01)

(58) Field of Classification Search
CPC ..... A61B 17/84; A61B 17/86; A61B 17/8625; A61B 17/863; A61B 17/864; A61B 17/866; F16B 35/041; F16B 33/02; F16B 25/0042; F16B 25/0052
See application file for complete search history.

(56) References Cited

U.S. PATENT DOCUMENTS

| | | |
|---|---|---|
| 7,850,717 B2 | 12/2010 | Dewey et al. |
| 2008/0134411 A1 | 6/2008 | Shapiro |
| 2008/0177331 A1 | 7/2008 | Perez-Cruet et al. |
| 2010/0042167 A1 | 2/2010 | Nebosky et al. |
| 2010/0094420 A1 | 4/2010 | Grohowski, Jr. |
| 2011/0172798 A1 | 7/2011 | Staiger et al. |
| 2014/0046381 A1 | 2/2014 | Asfora |
| 2015/0018956 A1 | 1/2015 | Steinmann et al. |
| 2015/0032159 A1 | 1/2015 | Beger et al. |

(Continued)

FOREIGN PATENT DOCUMENTS

| | | |
|---|---|---|
| CN | 104523342 A | 4/2015 |
| CN | 204337022 U | 5/2015 |

(Continued)

OTHER PUBLICATIONS

Tempco, et al., Spinal Implant and Method of Manufacture, U.S. Appl. No. 15/666,281, filed Aug. 1, 2017, 39 pages.

(Continued)

*Primary Examiner* — Julianna N Harvey
*Assistant Examiner* — Christina Negrellirodriguez

(57) ABSTRACT

A bone screw comprising a shaft having a wall, the wall including a minor diameter and at least one thread having an external thread form. The thread form including a first portion comprising a crest of the thread form and a second portion extends between a minor diameter of the thread form and the first portion. The first portion having a solid configuration relative to the second portion. In some embodiments, systems, spinal constructs, surgical instruments and methods are disclosed.

23 Claims, 6 Drawing Sheets

(56) References Cited

U.S. PATENT DOCUMENTS

| | | |
|---|---|---|
| 2015/0223907 A1 | 8/2015 | Kieser |
| 2015/0313658 A1* | 11/2015 | Kolb .................. A61B 17/8625 606/309 |
| 2016/0157908 A1 | 6/2016 | Cawley et al. |
| 2016/0367371 A1 | 12/2016 | de Beaubien et al. |
| 2017/0165077 A1 | 6/2017 | McDonnell |
| 2017/0245851 A1 | 8/2017 | Biedermann et al. |
| 2018/0028242 A1 | 2/2018 | Parekh et al. |
| 2018/0042702 A1 | 2/2018 | Stuebinger |

FOREIGN PATENT DOCUMENTS

| | | |
|---|---|---|
| CN | 204337069 U | 5/2015 |
| CN | 104758042 A | 7/2015 |
| CN | 104840243 A | 8/2015 |
| CN | 204581484 U | 8/2015 |
| CN | 204931871 U | 1/2016 |
| CN | 204931872 U | 1/2016 |
| CN | 105662621 A | 6/2016 |
| CN | 205698065 U | 11/2016 |
| CN | 106473787 A | 3/2017 |
| CN | 106580494 A | 4/2017 |
| CN | 106859792 A | 6/2017 |
| CN | 206576968 U | 10/2017 |
| CN | 206761724 U | 12/2017 |
| CN | 206761725 U | 12/2017 |
| CN | 206761797 U | 12/2017 |
| CN | 206761967 U | 12/2017 |
| FR | 3036945 A1 | 12/2016 |
| KR | 20140141463 A | 12/2014 |
| WO | 2008134411 A2 | 11/2008 |
| WO | 2014076157 A1 | 5/2014 |
| WO | 2017161115 A1 | 9/2017 |
| WO | 2017161121 A1 | 9/2017 |
| WO | 2017192853 A1 | 11/2017 |

OTHER PUBLICATIONS

Tempco, et al., System and Method of Manufacture for Spinal Implant, U.S. Appl. No. 15/666,305, filed Aug. 1, 2017, 39 pages.
Tempco, et al., System and Method of Manufacture for Spinal Implant, U.S. Appl. No. 15/889,355, filed Feb. 6, 2018, 41 pages.
BoneZone Magazine, Commercialization Solutions for the Orthopaedic Industry www.BONEZONEpub.com, vol. 16 Issue 3 | Aug. 2017, 2 pages.
AmorChem, Porous_screw, McGill, Research Institute McGill University Health Centre—Press Release 2012, 2 pages.
International Search Report and Written Opinion of the International Searching Authority, European Patent Office, PCT/US2019/031229 dated Aug. 23, 2019.

* cited by examiner

BONE SCREW AND METHOD OF MANUFACTURE

TECHNICAL FIELD

The present disclosure generally relates to medical devices for the treatment of spinal disorders, and more particularly to a spinal implant system having spinal implants manufactured by a method including a plurality of manufacturing techniques.

BACKGROUND

Spinal pathologies and disorders such as kyphosis, scoliosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including bone fasteners are often used to provide stability to a treated region. Such bone fasteners are traditionally manufactured using a medical machining technique. This disclosure describes an improvement over these prior technologies.

SUMMARY

In one embodiment, a bone screw is provided. The bone screw includes a shaft having a wall, the wall including a minor diameter and at least one thread having an external thread form. The thread form including a first portion comprising a crest of the thread form and a second portion extends between a minor diameter of the thread form and the first portion. The first portion having a solid configuration relative to the second portion. In some embodiments, systems, spinal constructs, surgical instruments and methods are disclosed.

In one embodiment, the bone screw comprises a shaft having a wall, the wall including a minor diameter and at least one thread having an external thread form. The thread form includes a first portion defining a leading edge of the thread form and a second portion defining a trailing edge of the thread form, the first portion having a solid configuration relative to the second portion.

In one embodiment, the bone screw comprises a shaft having a wall, the wall including a minor diameter and at least one thread having an external thread form. The thread form includes a first portion defining a trailing edge of the thread form and a second portion defining a leading edge of the thread form, the first portion having a solid configuration relative to the second portion.

BRIEF DESCRIPTION OF THE DRAWINGS

The present disclosure will become more readily apparent from the specific description accompanied by the following drawings, in which.

DETAILED DESCRIPTION

Figure 1:
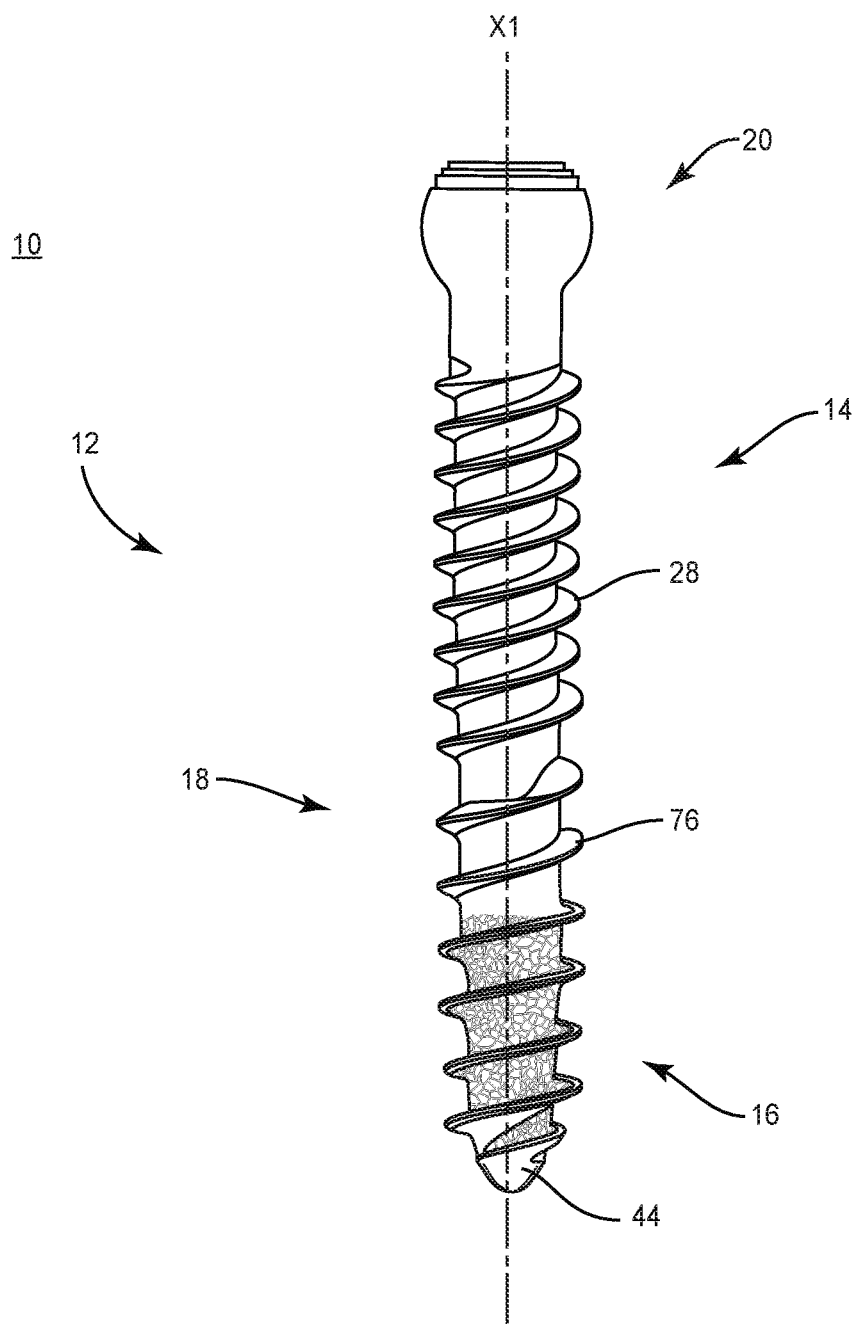
FIG. 1 is a side view of components of one embodiment of a system in accordance with the principles of the present disclosure.

The exemplary embodiments of a surgical system and related methods of use disclosed are discussed in terms of medical devices for the treatment of musculoskeletal disorders and more particularly, in terms of a variable structured spinal implant. In some embodiments, the spinal implant system includes a spinal implant comprising a variable structured bone screw.

In some embodiments, the spinal implant system of the present disclosure comprises a bone screw having variable structures, such as, for example, any combination of solid, roughened surfaces, porous surfaces, honeycomb filled and/or structure having a trabecular configuration. In some embodiments, the bone screw includes a thread form. In some embodiments, the thread form includes a solid portion along an edge and a porous and/or trabecular portion along a minor diameter of the thread form. In some embodiments, the solid edge of the thread form is configured to protect sensitive tissue. In some embodiments, the solid edge of the thread form is selectively positioned and configured to resist and/or prevent damage to surrounding anatomy, such as, for example, nerves, the dura, blood vessels or other sensitive tissue. In some embodiments, a leading edge of the thread form is solid, and the trailing edge of the thread form includes, for example, a porous, roughened or trabecular configuration. In some embodiments, the leading edge of the thread form includes, for example, a porous, roughened or trabecular structure configuration and the trailing edge of the thread form is solid. In some embodiments, a transition from one structure of the bone screw to another may be a gradual transition. In some embodiments, the bone screw includes sections having various structures.

In some embodiments, the spinal implant system of the present disclosure comprises a bone screw having variable structures and combines a manufacturing method, such as, for example, one or more traditional manufacturing features and materials and a manufacturing method, such as, for example, one or more additive manufacturing features and materials. In some embodiments, the bone screw is configured for engagement with cortical and/or cancellous bone. In some embodiments, captured cortical and/or cancellous bone is embedded within the bone screw as bone graft to facilitate promotion of bone growth and bone screw fusion. In some embodiments, external grafting materials or biologics may be prepacked within the bone screw.

In some embodiments, the spinal implant system of the present disclosure is configured to enhance fixation of bone screws with bone. In some embodiments, the spinal implant is configured to enhance the ability for a bone screw to be engaged with tissue.

In some embodiments, the spinal implant system comprises a spinal implant having a hybrid configuration that combines a manufacturing method, such as, for example, one or more traditional manufacturing features and materials and a manufacturing method, such as, for example, one or more additive manufacturing features and materials. In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing. In some embodiments, the spinal implant system comprises a spinal implant being manufactured by a fully additive process and grown or otherwise printed.

In some embodiments, the spinal implant system of the present disclosure comprises a spinal implant, such as, for example, a bone screw manufactured by combining traditional manufacturing methods and additive manufacturing methods. In some embodiments, the bone screw is manufactured by applying additive manufacturing material in areas where the bone screw can benefit from materials and properties of additive manufacturing. In some embodiments, traditional materials are utilized where the benefits of these materials, such as physical properties and cost, are superior to those resulting from additive manufacturing features and materials.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
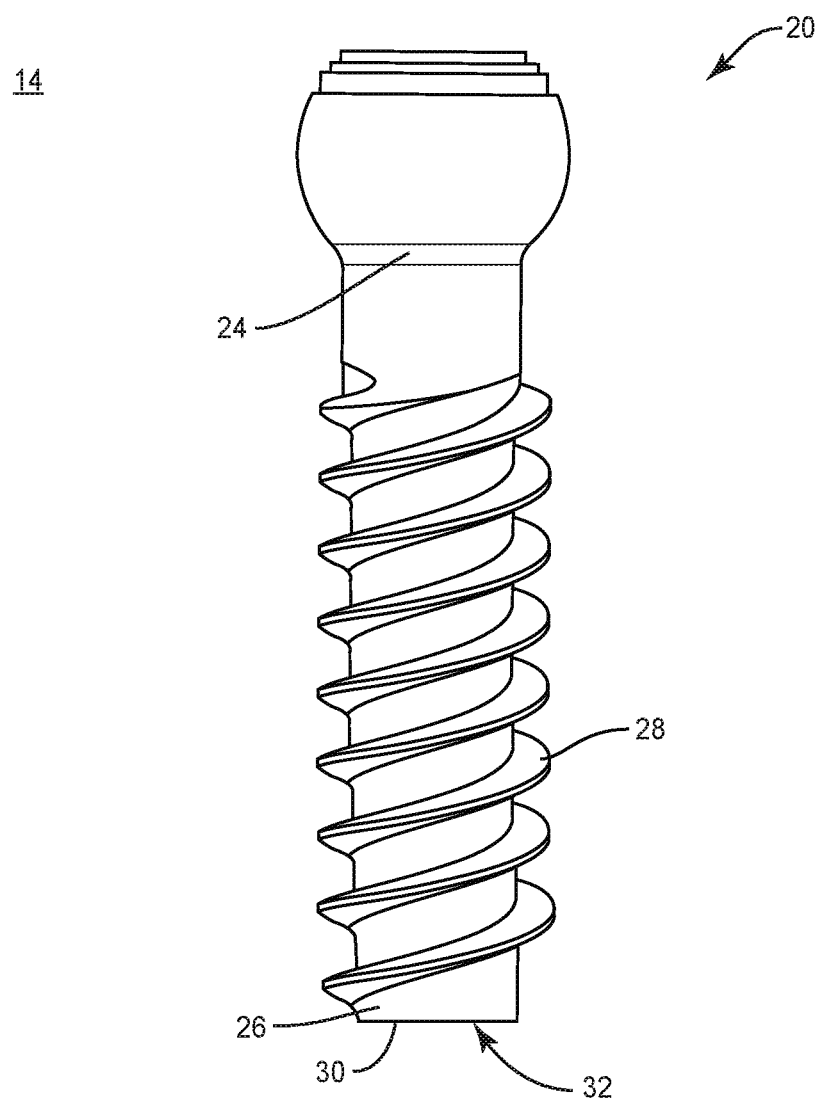
FIG. 2 is a side view of components of one embodiment of a system in accordance with the principles of the present disclosure.
Figure 3:
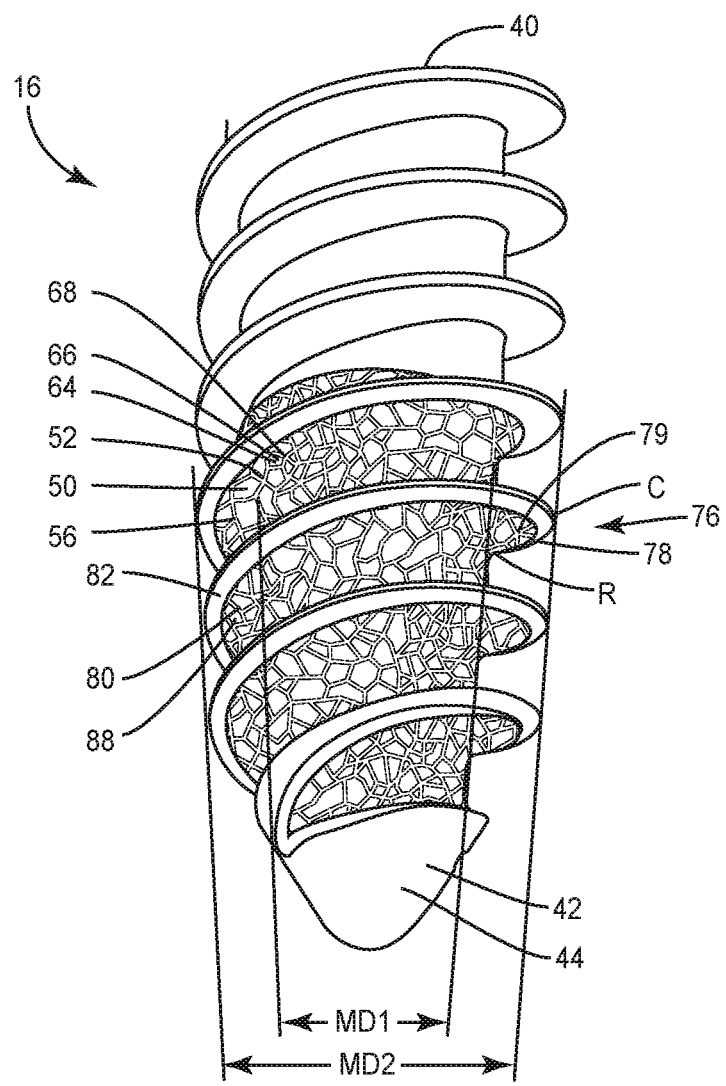
FIG. 3 is a break away perspective view of components of the system shown in FIG. 1.

The following discussion includes a description of a spinal implant, a method of manufacturing a spinal implant, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-3, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant comprising a bone fastener, such as, for example, a bone screw 12. Bone screw 12 includes a variable configuration that facilitates bone growth through bone screw 12 and/or fixation of bone screw 12 with tissue. In some embodiments, bone screw 12 includes one or more variable, alternate, different and/or transition portions to facilitate bone growth and/or fixation with tissue. In some embodiments, the portions of bone screw 12 can include one or more cavities, for example, one or more pathways, openings, lattice and/or scaffold. In some embodiments, bone screw 12 can include even, uninterrupted portions, portions that are continuous and without cavity and/or solid portions. In some embodiments, bone screw 12 can include roughened portions, porous portions, trabecular portions and/or honeycomb portions. For example, bone screw 12 can have a variable configuration including a thread having a solid portion, as described herein, and a shaft portion including a minor diameter, which has porous and/or trabecular configuration. In some embodiments, the solid portion protects sensitive tissue such as nerves, the dura and/or blood vessels. In another example, bone screw 12 can have a variable configuration including a thread having an entire leading edge that is solid and a trailing edge that is porous, roughened or trabecular in configuration. In another example, bone screw 12 can have a variable configuration including a thread having a trailing edge that is solid and a leading edge that is porous, roughened or trabecular in configuration. In some embodiments, bone screw 12 can have a variable configuration including one or more transition portions disposed between portions of the variable configuration, for example, tapered or gradual transition. In some embodiments, bone screw 12 allows bone growth therethrough such that bone is allowed to connect through bone screw 12.

Bone screw 12 defines a longitudinal axis X1. Bone screw 12 includes a screw shaft 18 having a proximal portion 14 and a distal portion 16. In some embodiments, bone screw 12 is manufactured by a manufacturing process to enhance fixation and/or facilitate bone growth, as described herein. In some embodiments, bone screw 12 is manufactured by an additive manufacturing method. In some embodiments, proximal portion 14 is fabricated by a first manufacturing method and distal portion 16 fabricated by a second manufacturing method to enhance fixation and/or facilitate bone growth, as described herein.

In some embodiments, the manufacturing method can include a traditional machining method, such as, for example, subtractive, deformative or transformative manufacturing methods. In some embodiments, the traditional manufacturing method may include cutting, grinding, rolling, forming, molding, casting, forging, extruding, whirling, grinding and/or cold working. In some embodiments, the traditional manufacturing method includes portion 14 being formed by a medical machining process. In some embodiments, medical machining processes can include use of computer numerical control (CNC) high speed milling machines, Swiss machining devices, CNC turning with living tooling and/or wire EDM 4th axis. In some embodiments, the manufacturing method for fabricating portion 14 includes a finishing process, such as, for example, laser marking, tumble blasting, bead blasting, micro blasting and/or powder blasting.

For example, portion 14 is formed by a manufacturing method, which includes feeding a wire, rod, bar, or wire or rod bar stock into a machine that cuts the wire at a designated length to form a screw blank and then forms a head of the screw blank into a selected configuration. Portion 14 is manufactured to include a head 20 and a portion of screw shaft 18. Portion 14 extends between an end 24 and an end 26. End 24 includes head 20.

Portion 14 includes threads 28, which are fabricated by traditional machining methods, as described herein. Threads 28 extend along all or a portion of portion 14. Threads 28 are oriented with portion 14 and disposed for engagement with tissue. In some embodiments, threads 28 include a fine, closely-spaced configuration and/or shallow configuration to facilitate and/or enhance engagement with tissue. In some embodiments, threads 28 include a smaller pitch or more thread turns per axial distance to provide a stronger fixation with tissue and/or resist loosening from tissue. In some embodiments, threads 28 include an increased pitch and an equal lead between thread turns. In some embodiments, threads 28 are continuous along portion 14. In some embodiments, threads 28 are continuous along shaft 18 via a second manufacturing method, as described herein. In some embodiments, threads 28 may be intermittent, staggered, discontinuous and/or may include a single thread turn or a plurality of discrete threads. In some embodiments, other penetrating elements may be located on and/or manufactured with portion 14, such as, for example, a nail configuration, barbs, expanding elements, raised elements, ribs, and/or spikes to facilitate engagement of portion 14 with tissue.

End 26 includes a surface 30 that defines a distal end 32. In some embodiments, surface 30 may be disposed along a length of portion 14 or at a distalmost surface of portion 14. In some embodiments, distal end 32 extends perpendicular to axis X1. In some embodiments, distal end 32 may be disposed in various orientations relative to axis X1, such as, for example, transverse and/or at angular orientations, such as acute or obtuse. In one embodiment, distal end 32 is disposed at an acute angular orientation relative to axis X1.

Distal end 32 is configured for providing a fabrication platform for forming portion 16 thereon with an additive manufacturing method, as described herein. Distal end 32 has a substantially planar configuration for material deposition and/or heating during an additive manufacturing process for fabricating portion 16 onto distal end 32. In some embodiments, all or only a portion of distal end 32 may have alternate surface configurations, such as, for example, angled, irregular, uniform, non-uniform, offset, staggered, tapered, arcuate, undulating, mesh, porous, semi-porous, dimpled, pointed and/or textured. In some embodiments, distal end 32 may include a nail configuration, barbs, expanding elements, raised elements, ribs, and/or spikes to provide a fabrication platform for forming portion 16 thereon with an additive manufacturing method, as described herein. In some embodiments, all or only a portion of distal end 32 may have alternate cross section configurations, such as, for example, oval, oblong triangular, square, polygonal, irregular, uniform, non-uniform, offset, staggered, and/or tapered.

Portion 16 is fabricated with a second manufacturing method by disposing a material onto distal end 32, as described herein. Portion 16 is configured for fabrication on distal end 32 such that portion 16 is fused with surface 30. Portion 16 is formed on distal end 32 by an additive manufacturing method. Portion 16 is formed on distal end 32 to extend between an end 40 and end 42 according to instructions received from the computer and processor, and end 40 is fused with surface 30. End 42 includes a distal tip 44.

Portion 16 is fabricated according to instructions received from the computer and processor based on the digital rendering and/or data of the selected configuration, via the additive manufacturing process described herein to include a thread 76 that extends between end 40 and distal tip 44. Thread 76 has a variable configuration, as described herein, and includes an external thread form 78. Thread form 78 has a flank 79 extending between a root R and a crest C.

Portion 16 includes a wall 50 having a surface 52. In some embodiments, wall 50 extends circumferentially to define portion 16. In some embodiments, wall 50 is disposed about a solid inner core. In some embodiments, wall 50 defines a thickness, which may be uniform, undulating, tapered, increasing, decreasing, variable, offset, stepped, arcuate, angled and/or staggered. In some embodiments, surface 52 may be rough, textured, porous, semi-porous, dimpled, knurled, toothed, grooved and/or polished.

Surface 52 includes a non-solid configuration, such as, for example, a lattice 56. In some embodiments, the non-solid configuration may include a porous structure and/or a trabecular configuration. Disclosures herein involving a lattice, or other particular type of non-solid structure, are meant to disclose at the same time analogous embodiments in which other non-solid structure in addition or instead of the particular type of structure.

In various embodiments, the non-solid configuration is configured to provide one or a plurality of pathways to facilitate bone through growth within, and in some embodiments all of the way through, from one surface to an opposite surface of bone screw 12. Lattice 56 extends along surface 52 of portion 16 between end 40 and distal tip 44. In some embodiments, lattice 56 extends along all or a portion of an inner core of bone screw 12. In some embodiments, lattice 56 extends circumferentially about a minor diameter of bone screw 12. Lattice 56 transitions to and extends along root R of thread form 78. In some embodiments, lattice 56 extends along all or a portion of flank 79 of thread form 78.

In some embodiments, lattice 56 may include one or more portions, layers and/or substrates. In some embodiments, one or more portions, layers and/or substrates of lattice 56 may be disposed side by side, offset, staggered, stepped, tapered, end to end, spaced apart, in series and/or in parallel. In some embodiments, lattice 56 defines a thickness, which may be uniform, undulating, tapered, increasing, decreasing, variable, offset, stepped, arcuate, angled and/or staggered. In some embodiments, one or more layers of lattice 56 are disposed in a side by side, parallel orientation within wall 50. Lattice 56 includes one or more layers of a matrix of material.

In some embodiments, lattice 56 includes a plurality of nodes 64 and openings 66, which can be disposed in rows and columns, and/or in a random configuration. In some embodiments, nodes 64 and openings 66 are disposed in a series orientation. In some embodiments, nodes 64 and openings 66 are disposed in a parallel orientation. In some embodiments, lattice 56 may form a rasp-like configuration. In some embodiments, lattice 56 is configured to engage tissue, such as, for example, cortical bone and/or cancellous bone, such as, to cut, shave, shear, incise and/or disrupt such tissue. In some embodiments, all or a portion of lattice 56 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, lattice 56 may be rough, textured, porous, semi-porous, dimpled, knurled, toothed, grooved and/or polished to facilitate engagement and cutting of tissue. In some embodiments, lattice 56 forms a tunnel configured to guide, drive and/or direct the cut tissue into openings 66 to facilitate fusion of bone screw 12 with tissue, such as, for example, vertebrae.

A surface 68 of lattice 56 is configured to engage tissue, such as, for example, cortical bone and/or cancellous bone, such as, to cut, shave, shear, incise and/or disrupt such tissue. In some embodiments, all or a portion of surface 68 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, surface 68 may be rough, textured, porous, semi-porous, dimpled, knurled, toothed, grooved and/or polished to facilitate engagement and cutting of tissue.

Flank 79 has a variable configuration and includes a portion 80 and a portion 82 to facilitate bone growth and/or fixation with tissue. Portion 80 extends circumferentially about root R and/or a minor diameter MD1. Portion 80 includes a lattice configuration to facilitate fusion of bone screw 12 with tissue, as described herein. Portion 80 transitions from lattice 56 such that wall 50 and portion 82 are homogenous. In some embodiments, portion 80 includes a trabecular configuration. In some embodiments, the trabecular configuration may include a density similar to cancellous or cortical bone tissue. In some embodiments, portion 80 includes a porous configuration. In some embodiments, the porous configuration may include a range of porosity over a wide range of effective pore sizes. In some embodiments, the porous configuration of portion 16 may have macroporosity, mesoporosity, microporosity and nanoporosity.

A surface 88 of the lattice of portion 80 is configured to engage tissue, such as, for example, cortical bone and/or cancellous bone, such as, to cut, shave, shear, incise and/or disrupt such tissue. In some embodiments, all or a portion of surface 88 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, surface 88 may be rough, textured, porous, semi-porous, dimpled, knurled, toothed, grooved and/or polished to facilitate engagement and cutting of tissue.

Portion 82 defines an even, uninterrupted edge surface of thread form 78, and includes an even, solid surface relative to portion 80, which provides a variable configuration of thread form 78. Portion 82 extends along crest C and/or a major diameter MD2 forming an edge surface of thread form 78 that transitions from portion 80 and is configured to resist and/or prevent damage to tissue during insertion and/or engagement of bone screw 12 with tissue. Portion 82 is configured to resist and/or prevent damage to nerves, the dura and/or blood vessels. In some embodiments, portion 82 is continuous without any openings and/or cavities. In some embodiments, portion 82 includes a material having a closely compacted structure. In some embodiments, portion 82 includes a solid configuration, which may include a range of density including 0.5 through 10.5 grams per cubic centimeter. In some embodiments, portion 82 includes a density that is greater than a density of portion 80. The portions 80, 82, and an interface between them, can have any of a wide variety of configurations, including respective sizes, shapes, and positionings. In various embodiments, for instance, the portion 82 extends inward from the crest C to make up about half of the thread form 78, and portion 80 makes up about half of the thread form. In various embodiments, the interface is located such that the portion 82 takes up more or less than half of the thread form 78, such as by comprising between about 50% and 60% of the thread form 78, greater than about 60% of the thread form 78, between about 40% and 50% of the thread form 78, or less than about 40% of the thread form 78, as just a few examples.

For example, manipulation of bone screw 12, including rotation and/or translation causes surfaces 68, 88 to cut tissue and/or shave bone such that the cut tissue is guided and/or directed into portion 80 and lattice 56 to enhance the function of bone screw 12, such as, for example, by facilitating engagement with tissue. During manipulation, the even, solid configuration of edge 84 resists and/or prevent damage to tissue. In some embodiments, the tissue is imbedded with portion 80 and lattice 56 promotes bone growth and enhance fusion of bone screw 12. The variable structure of portions 80, 82 facilitates bone growth and/or fixation of bone screw 12 with tissue.

In some embodiments, thread 76 is fabricated to include a fine, closely-spaced and/or shallow configuration to facilitate and/or enhance engagement with tissue. In some embodiments, thread 76 is fabricated to include an increased pitch and an equal lead between thread turns than thread 28, as shown in FIG. 1. In some embodiments, thread 76 is fabricated to include a smaller pitch or more thread turns per axial distance than thread 28 to provide a stronger fixation with tissue and/or resist loosening from tissue. In some embodiments, thread 76 is fabricated to be continuous along portion 16. In some embodiments, thread 76 is fabricated to be continuous along portion 16. In some embodiments, thread 76 is fabricated to be intermittent, staggered, discontinuous and/or may include a single thread turn or a plurality of discrete threads. In some embodiments, portion 16 is fabricated to include penetrating elements, such as, for example, a nail configuration, barbs, expanding elements, raised elements, ribs, and/or spikes. In some embodiments, thread 76 is fabricated to be self-tapping or intermittent at distal tip 44. In some embodiments, distal tip 44 may be rounded. In some embodiments, distal tip 44 may be self-drilling. In some embodiments, distal tip 44 includes a solid outer surface.

In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing. In some embodiments, portion 16 is manufactured by additive manufacturing, as described herein, and mechanically attached with surface 30 by, for example, welding, threading, adhesives and/or staking.

In one embodiment, one or more manufacturing methods for fabricating distal portion 16, proximal portion 14 and/or other components of bone screw 12 include imaging patient anatomy with imaging techniques, such as, for example, x-ray, fluoroscopy, computed tomography (CT), magnetic resonance imaging (MRI), surgical navigation, bone density (DEXA) and/or acquirable 2-D or 3-D images of patient anatomy. Selected configuration parameters of distal portion 16, proximal portion 14 and/or other components of bone screw 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of distal portion 16 determined based on patient anatomy and the surgical treatment. In some embodiments, the implant material includes a selected porosity of distal portion 16, as described herein. In some embodiments, the selected configuration parameters of distal portion 16, proximal portion 14 and/or other components of bone screw 12 are patient specific. In some embodiments, the selected configuration parameters of distal portion 16, proximal portion 14 and/or other components of bone screw 12 are based on generic or standard configurations and/or sizes and not patient specific. In some embodiments, the selected configuration parameters of distal portion 16, proximal portion 14 and/or other components of bone screw 12 are based on one or more configurations and/or sizes of components of a kit of spinal implant system 10 and not patient specific.

For example, based on one or more selected configuration parameters, as described herein, a digital rendering and/or data of a selected distal portion 16, proximal portion 14 and/or other components of bone screw 12, which can include a 2-D or a 3-D digital model and/or image, is collected, calculated and/or determined, and generated for display from a graphical user interface, as described herein, and/or storage on a database attached to a computer and a processor (not shown), as described herein. In some embodiments, the computer provides the ability to display, via a monitor, as well as save, digitally manipulate, or print a hard copy of the digital rendering and/or data. In some embodiments, a selected distal portion 16, proximal portion 14 and/or other components of bone screw 12 can be designed virtually in the computer with a CAD/CAM program, which is on a computer display. In some embodiments, the processor may execute codes stored in a computer-readable memory medium to execute one or more instructions of the computer, for example, to transmit instructions to an additive manufacturing device, such as, for example, a 3-D printer. In some embodiments, the database and/or computer-readable medium may include RAM, ROM, EPROM, magnetic, optical, digital, electromagnetic, flash drive and/or semiconductor technology. In some embodiments, the processor can instruct motors (not shown) that control movement and rotation of spinal implant system 10 components, for example, a build plate, distal end 32 and/or laser emitting devices, as described herein.

Portion 14 is fabricated with threads 28 by a first manufacturing method, as described herein. Portion 14 is connected with a part, such as, for example, a build plate in connection with an additive forming process and a second manufacturing method for fabricating distal portion 16. Portion 16 is built up layer by layer and the melting process is repeated slice by slice, layer by layer, until the final layer of a material is melted and portion 16 is complete. Portion 16 is formed on distal end 32 to extend between an end 40 and end 42 according to instructions received from the computer and processor, and end 40 is fused with surface 30. In some embodiments, the material is subjected to direct metal laser sintering (DMLS®), selective laser sintering (SLS), fused deposition modeling (FDM), or fused filament fabrication (FFF), or stereolithography (SLA).

In some embodiments, portion 16 is fabricated in a configuration having a porosity via the additive manufacturing method, as described herein. In some embodiments, portion 16 is fabricated having a porosity with a porogen that is spheroidal, cuboidal, rectangular, elongated, tubular, fibrous, disc-shaped, platelet-shaped, polygonal or a mixture thereof. In some embodiments, a porosity of portion 16 is based on a plurality of macropores, micropores, nanopores structures and/or a combination thereof.

In some embodiments, bone screw 12 includes an implant receiver (not shown) connectable with head 20. In some embodiments, bone screw 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw. In some embodiments, the implant receiver can be attached by manual engagement and/or non-instrumented assembly, which may include a practitioner, surgeon and/or medical staff grasping the implant receiver and shaft 18 and forcibly snap or pop fitting the components together. In some embodiments, spinal implant system 10 comprises a kit including a plurality of bone screws 12 of varying configuration, as described herein. In some embodiments, bone screw 12 is selected from the kit and employed with a treatment at the surgical site.

In one embodiment, bone screw 12 is fabricated to define a passageway through all or a portion of shaft 18 such that bone screw 12 includes a cannulated configuration and a plurality of lateral fenestrations in communication with the passageway.

In assembly, operation and use, spinal implant system 10 is employed to treat an affected section of vertebrae. A medical practitioner obtains access to a surgical site including the vertebrae in any appropriate manner, such as through incision and retraction of tissues. The components of surgical system 10 including bone screw 12 are employed to augment a surgical treatment. Bone screw 12 can be delivered to a surgical site as a pre-assembled device or can be assembled in situ. Spinal implant system 10 may be may be completely or partially revised, removed or replaced.

Surgical system 10 may be used with surgical methods or techniques including open surgery, mini-open surgery, minimally invasive surgery and percutaneous surgical implantation, whereby the vertebrae is accessed through a mini-incision, or sleeve that provides a protected passageway to the area. Once access to the surgical site is obtained, a surgical treatment, for example, corpectomy and/or discectomy, can be performed for treating a spine disorder.

Bone screw 12 is connected with a surgical instrument, such as, for example, a driver (not shown) and is delivered to the surgical site. Bone screw 12 is manipulated including rotation and/or translation for engagement with cortical bone and/or cancellous bone. Manipulation causes surfaces 68, 88 to cut tissue and/or shave bone such that the cut tissue is guided and/or directed into portion 80 and lattice 56. During manipulation, the even, solid configuration of portion 82 resists and/or prevent damage to tissue. The tissue becomes imbedded with portion 80 and lattice 56 to promote bone growth and enhance fusion of bone screw 12 to resist and/or prevent toggle. The variable structure of portions 80, 82 facilitates bone growth and/or fixation of bone screw 12 with tissue.

Figure 4:
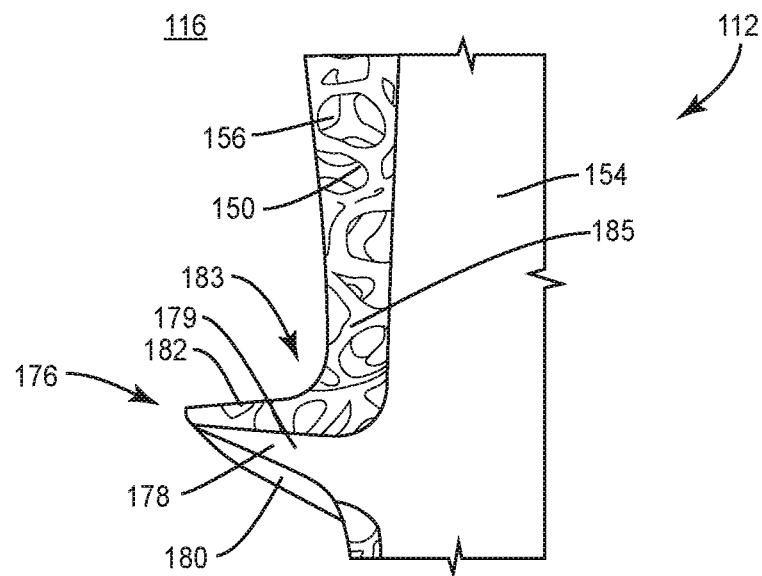
FIG. 4 is a break away, side view of components of one embodiment of a system in accordance with the principles of the present disclosure.

In one embodiment, as shown in FIG. 4, spinal implant system 10, similar to the systems and methods described herein, includes a bone screw 112, similar to bone screw 12 described herein. Bone screw 112 includes portion 14 (FIG. 1), as described herein, and a portion 116.

Portion 116 includes a wall 150, similar to wall 50 described herein, having a non-solid configuration, as described herein, such as, for example, a lattice 156, similar to lattice 56 described herein. Wall 150 extends about an inner core 154 that in some embodiments is solid. Portion 116 includes a thread 176. Thread 176 has a variable configuration, as described herein, and includes an external thread form 178. Thread form 178 includes a flank 179, similar to flank 79 as described herein.

Flank 179 has a variable configuration and includes a portion defining a trailing or lagging edge 182 and a portion defining a leading edge 180 to facilitate bone growth and/or fixation with tissue. In some embodiments, a ratio of trailing edge 182 to leading edge 180 is 50:50, such that trailing edge 182 makes up approximately half of thread form 178 and leading edge 180 makes up approximately half of thread form 178. In some embodiments, the ratio of trailing edge 182 to leading edge 180 can be varied.

Trailing edge 182 includes a non-solid configuration, such as, for example, a lattice configuration to facilitate fusion of bone screw 112 with tissue, as described herein. In various embodiments, flank 179 transitions at portion 183 to a portion 185 of wall 150 such that trailing edge 182 and portion 185 are homogenous. Trailing edge 182 connects seamlessly to portion 185, between threads of thread form 178. Portion 185 includes a non-solid structure. In some embodiments, trailing edge 182 includes a trabecular configuration.

Leading edge 180 defines an even, uninterrupted edge surface of thread form 178, and includes an even, solid surface relative to trailing edge 182, which provides a variable configuration of thread form 178. In various embodiments, leading edge 180 transitions from a similarly solid inner core 154. Leading edge 180 is configured to resist and/or prevent damage to tissue during insertion and/or engagement of bone screw 112 with tissue. In some embodiments, leading edge 180 is continuous without any openings and/or cavities, as described herein. The portions 180, 182 can have any of a wide variety of configurations, including respective sizes, shapes, and positionings. In various embodiments, for instance, the leading portion 180 extends to the thread crest, or tip. In other embodiments, the trailing portion 182 extends to the tread crest. A designer of the screw 112 can locate and shape an interface between the leading and trailing portions 180, 182 in any manner. The interface can be located such that, for instance, the leading portion 180 and the trailing portion 182 each make up about half of the thread form 178. In various embodiments, the interface is located such that the leading portion 180 takes up more or less than half of the thread form 178, such as by comprising between about 50% and 60% of the thread form 178, greater than about 60% of the thread form 178, between about 40% and 50% of the thread form 178, or less than about 40% of the thread form 178, as just a few examples.

In some embodiments, portion 116 is formed on distal end 32 of portion 14 (FIG. 1) by an additive manufacturing method, as described herein. In some embodiments, portion 116 is fabricated according to instructions received from the computer and processor based on the digital rendering and/or data of the selected configuration, via the additive manufacturing process, as described herein. Portion 116 is configured for fabrication on distal end 32 such that portion 116 is fused with surface 30 of portion 14, as described herein.

Figure 5:
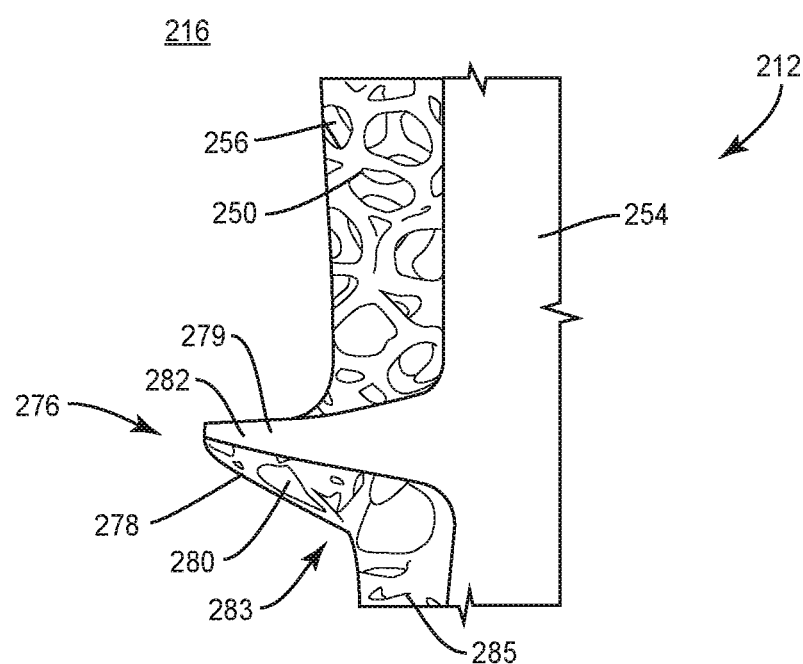
FIG. 5 is a break away, side view of components of one embodiment of a system in accordance with the principles of the present disclosure.

In one embodiment, as shown in FIG. 5, spinal implant system 10, similar to the systems and methods described herein, includes a bone screw 212, similar to bone screws 12 or 112, described herein. Bone screw 212 includes portion 14 (FIG. 1), as described herein, and a portion 216.

Portion 216 includes a wall 250, similar to wall 50 described herein, having a non-solid configuration, as described herein, such as, for example, a lattice 256, similar to lattice 56 described herein. In various embodiments, wall 250 extends about a solid inner core 254. Portion 216 includes a thread 276. Thread 276 has a variable configuration, as described herein, and includes an external thread form 278. Thread form 278 includes a flank 29, similar to flank 79 as described herein.

Flank 279 has a variable configuration and includes a trailing edge 282 and a leading edge 280 to facilitate bone growth and/or fixation with tissue. Trailing edge 282 defines an even, uninterrupted edge surface of thread form 278, and includes an even, solid surface relative to leading portion 280, which provides a variable configuration of thread form 278. In various embodiments, trailing edge 282 transitions from a similarly sold inner core 254. In some embodiments, trailing edge 282 is continuous without any openings and/or cavities, as described herein.

Leading edge 280 includes a non-solid configuration, such as, for example, a lattice configuration to facilitate fusion of bone screw 212 with tissue, as described herein. In various embodiments, flank 279 transitions at portion 283 to a portion 285 of wall 250 such that leading edge 182 and portion 285 are homogenous. Flank 279 connects seamlessly to portion 285, between threads of thread form 278. Portion 285 includes a non-solid structure. In some embodiments, leading edge 280 includes a trabecular configuration. The portions 280, 282 can have any of a wide variety of configurations, including respective sizes, shapes, and positionings. In various embodiments, for instance, the leading portion 280 extends to the thread crest, or tip. In other embodiments, the trailing portion 282 extends to the tread crest. A designer of the screw 212 can locate and shape an interface between the leading and trailing portions 280, 282 in any manner. The interface can be located such that, for instance, the leading portion 280 and the trailing portion 282 each make up about half of the thread form 278. In various embodiments, the interface is located such that the leading portion 280 takes up more or less than half of the thread form 278, such as by comprising between about 50% and 60% of the thread form 278, greater than about 60% of the thread form 278, between about 40% and 50% of the thread form 278, or less than about 40% of the thread form 278, as just a few examples.

In some embodiments, portion 216 is formed on distal end 32 of portion 14 (FIG. 1) by an additive manufacturing method, as described herein. In some embodiments, portion 216 is fabricated according to instructions received from the computer and processor based on the digital rendering and/or data of the selected configuration, via the additive manufacturing process, as described herein. Portion 216 is configured for fabrication on distal end 32 such that portion 216 is fused with surface 30 of portion 14, as described herein.

Figure 6:
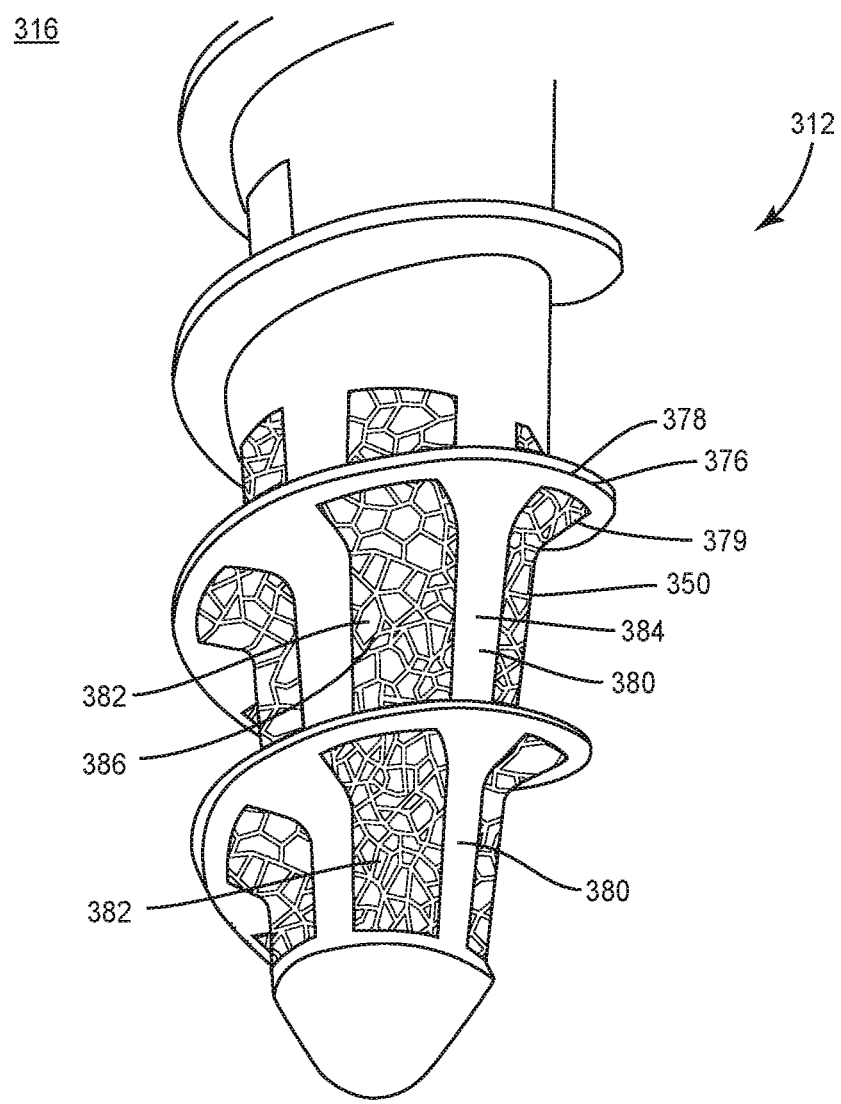
FIG. 6 is a break away perspective view of components of one embodiment of a system in accordance with the principles of the present disclosure.
Figure 7:
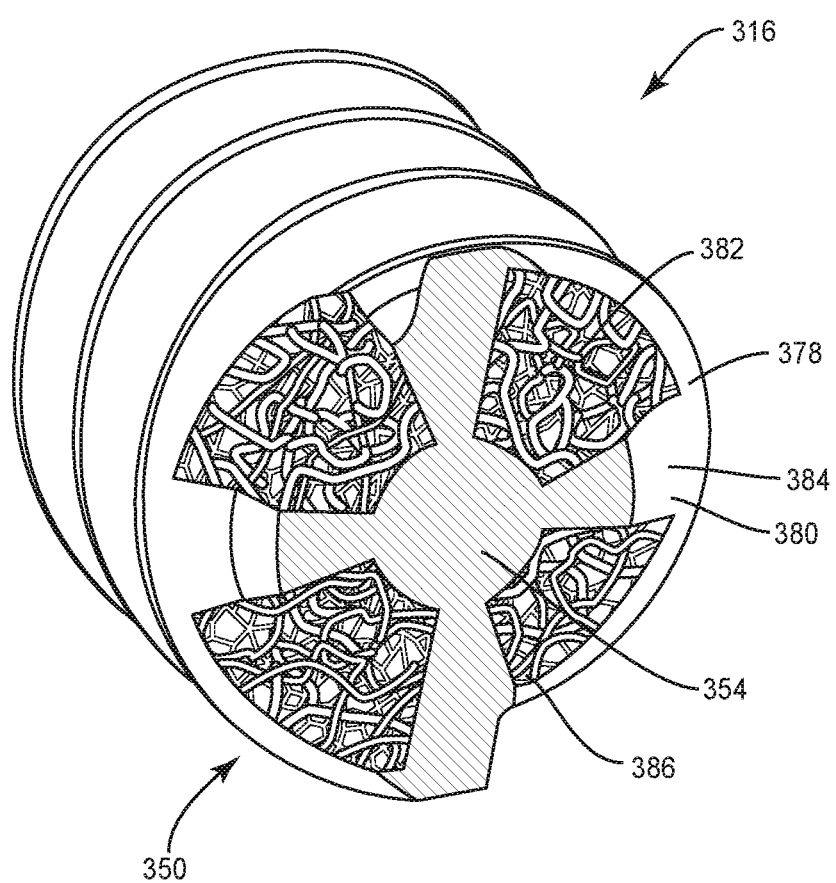
FIG. 7 is a cross section, perspective view of components of the system shown in FIG. 6.

In one embodiment, as shown in FIGS. 6 and 7, spinal implant system 10, similar to the systems and methods described herein, includes a bone screw 312, similar to bone screw 12 described herein. Bone screw 312 includes portion 14, as described herein, and a portion 316.

Portion 316 includes a variable configuration, as described herein, and includes a wall 350. Wall 350 extends about a solid inner core 354. Portion 316 includes a thread 376 having an external thread form 378. Thread form 378 includes a flank 379, similar to flank 79 as described herein.

Wall 350 has a variable configuration and includes a portion 380 and a portion 382 to facilitate bone growth and/or fixation with tissue. Portion 380 includes a plurality of struts 384 that extend along portion 316. Struts 384 are circumferentially disposed about portion 316 and define a cavity 386 therebetween. Struts 384 extend along all or a portion of flank 379, which provides a variable configuration of thread form 378. Struts 384 includes an even, solid surface relative to portion 382, as described herein. Struts 374 transition from inner core 354 to reinforce thread 376 to resist both torsional strength as well as aiding with pull-out strength.

Portion 382 includes a non-solid configuration, as described herein, such as, for example, a lattice 386, similar to lattice 56 as described herein. Portion 382 is disposed with cavities 386 such that lattice 386 is non-continuous along portion 316 forming the variable configuration of wall 350. Lattice 386 extends along all or a portion of flank 379, which provides a variable configuration of thread form 378 with struts 384. In some embodiments, portion 382 includes a trabecular configuration, as described herein.

In some embodiments, portion 316 is formed on distal end 32 by an additive manufacturing method, as described herein. In some embodiments, portion 316 is fabricated according to instructions received from the computer and processor based on the digital rendering and/or data of the selected configuration, via the additive manufacturing process, as described herein. Portion 316 is configured for fabrication on distal end 32 such that portion 316 is fused with surface 30, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone screw comprising:
a shaft having a wall, the wall including a minor diameter and at least one thread having an external thread form, the thread form comprising a plurality of threads, at least one of the threads including a first portion comprising a crest of the thread form and a second portion extending from the first portion of one of the threads to a root of an adjacent one of the threads, the first portion having a solid configuration relative to the second portion,
wherein the second portion extends continuously from a root of the one of the threads to the root of the adjacent one of the threads.

2. A bone screw as recited in claim 1, wherein the first portion is continuous and without cavity.

3. A bone screw as recited in claim 1, wherein the second portion includes a lattice configured to promote bone growth through the second portion in use of the bone screw.

4. A bone screw as recited in claim 1, wherein the second portion includes a porous configuration to promote bone growth through the second portion in use of the bone screw.

5. A bone screw as recited in claim 1, wherein the first portion includes an even, uninterrupted edge surface of the thread form.

6. A bone screw as recited in claim 1, wherein the wall includes a plurality of struts circumferentially disposed about a distal portion of the shaft.

7. A bone screw as recited in claim 6, wherein the shaft includes a solid inner core connected with the struts and a trabecular configuration being disposed about the core.

8. A bone screw as recited in claim 1, wherein the shaft includes a proximal portion, a distal portion including the first and second portions and a distal tip.

9. A bone screw as recited in claim 1, wherein the shaft includes a proximal portion, a distal portion including the first and second portions and a distal tip, and the distal portion is fabricated from an additive manufacturing method including heating a material in a layer by layer formation.

10. A bone screw as recited in claim 1, wherein the bone screw is manufactured by an additive manufacturing method.

11. A bone screw as recited in claim 1, wherein the shaft includes a proximal portion and a distal portion including the first and second portions, the proximal portion being fabricated by a first manufacturing method, the distal portion being fabricated by a second manufacturing method, the second manufacturing method being different than the first manufacturing method.

12. A bone screw as recited in claim 1, wherein the second portion has a non-solid configuration.

13. A bone screw as recited in claim 1, wherein the second portion has a non-solid configuration, the non-solid configuration comprising a plurality of pathways configured to facilitate bone growth therein.

14. A bone screw comprising:
a shaft extending between opposite proximal and distal ends, the shaft having a wall, the wall including a minor diameter and at least one thread having an external thread form,
the thread form comprising a plurality of threads, at least one of the threads including a first portion defining a leading edge of the thread form and a second portion defining a trailing edge of the thread form, the first portion having a solid configuration relative to the second portion, the leading edge facing the proximal end, the trailing edge facing the distal end,
wherein the wall includes a plurality of struts circumferentially disposed about a distal portion of the shaft, and
wherein the shaft includes a solid inner core connected with the struts and a trabecular configuration being disposed about the core.

15. A bone screw as recited in claim 14, wherein the first portion includes an even, uninterrupted surface and the second portion includes a trabecular configuration.

16. A bone screw as recited in claim 14, wherein the first portion is continuous and without cavity.

17. A bone screw as recited in claim 14, wherein the second portion includes a lattice configuration.

18. A bone screw as recited in claim 14, wherein the second portion has a non-solid structure and connects seamlessly to a side portion of the wall, between threads of the thread form, the side portion having the non-solid structure.

19. A bone screw as recited in claim 14, wherein the first portion makes up about half of the thread form and the second portion makes about half of the thread form.

20. A bone screw as recited in claim 14, wherein the shaft includes a proximal portion, a distal portion including the first and second portions and a distal tip.

21. A bone screw as recited in claim 14, wherein the distal portion is fabricated from an additive manufacturing method including adding a material in a layer by layer formation.

22. A bone screw comprising:
a shaft extending between opposite proximal and distal ends, the shaft having a wall, the wall including a minor diameter and at least one thread having an external thread form,
the thread form comprising a plurality of threads, at least one of the threads including first portion defining a trailing edge of the thread form and a second portion defining a leading edge of the thread form, the first portion having a solid configuration relative to the second portion, the leading edge facing the proximal end, the trailing edge facing the distal end,
wherein the second portion extends continuously from a root of the one of the threads to a root of an adjacent one of the threads.

23. A bone screw as recited in claim 14, wherein the second portion extends continuously from a root of one of the threads to a root of an adjacent one of the threads.

* * * * *